United States Patent [19]
Stoller et al.

[11] 4,051,174
[45] Sept. 27, 1977

[54] ISOMERIZATION PROCESS

[75] Inventors: Hansjörg Stoller, Reinach; Hans Peter Wagner, Itingen, both of Switzerland

[73] Assignee: Hoffmann-La Roche Inc., Nutley, N.J.

[21] Appl. No.: 498,161

[22] Filed: Aug. 16, 1974

[30] Foreign Application Priority Data

Aug. 21, 1973 Switzerland ........................ 11994/73
July 3, 1974 Switzerland ......................... 9101/74
July 18, 1974 Switzerland ......................... 9879/74

[51] Int. Cl.² .................... C07C 67/00; C07C 45/00; C07C 41/00; C07C 29/00
[52] U.S. Cl. ................................... 560/234; 260/598; 260/617 A; 260/413; 260/611 V; 260/240 H; 260/405.6; 260/404; 542/429; 560/104

[58] Field of Search ................... 260/598, 611 V, 491, 260/617 V, 240 H, 514, 338, 488, 469, 468, 557, 413, 617 A, 476 R, 405.6, 404

[56] References Cited

U.S. PATENT DOCUMENTS 2,849,507  8/1958  Isler et al. ........................ 260/666 C
3,441,623  4/1969  Surmatis ........................... 260/666 C

OTHER PUBLICATIONS

Bergman, Isomerism and Isomerization (1948), pp. 27–50.
Cramer et al., J.A.C.S., vol. 88 (1966), pp. 3534–3539.

*Primary Examiner*—Bernard Helfin
*Attorney, Agent, or Firm*—Samuel L. Welt; George M. Gould; William H. Epstein

[57]           ABSTRACT

A process for isomerizing vitamin A and derivatives thereof utilizing either palladium or a palladium containing compound as a catalyst.

15 Claims, No Drawings

ISOMERIZATION PROCESS

BACKGROUND OF THE INVENTION

In vitamin A, for example, and in its alkanoyl esters, the five conjugated double-bonds all have the trans-configuration. Of all the isomers, the all-trans vitamin A or its alkanoyl esters possess by far the greatest biological activity and are accordingly used almost exclusively in human and animal nutrition. Present commercial vitamin A preparations are almost exclusively of the synthetic type. However, the known and used processes for the manufacture of vitamin A and compositions thereof do not yield the pure all-trans compounds, but rather yield mixtures of various isomers containing more or less large amounts of the all-trans isomer. Therefore, there is the problem of isomerising the various isomers into the all-trans compound. This problem is especially acute since there is no good procedure for isomerizing the 9-cis compound into the all-trans compound. The problem of isomerism which arises is to achieve the highest possible yields of all-trans compounds and, also, since total cis-trans conversion is not possible, to obtain mixtures from which the all-trans isomer can be isolated in the easiest manner possible. The method most widely used has been isomerisation with iodine in the presence of pyridine. This method suffers from the disadvantage that only the 11-cis and 13-cis as well as 11,13-di-cis isomers, but not 9-cis or 9,13-di-cis isomers, can be converted into all-trans compounds.

The problem to be solved accordingly consists in finding an isomerisation process whereby there can be obtained, from the pure isomers or from any isomer mixtures thereof, a mixture which has the highest possible content of all-trans compound or a mixture from which the all-trans isomer can be readily isolated in the purest possible form.

SUMMARY OF THE INVENTION

In accordance with this invention, it has been discovered that an isomeric composition containing a compound of the formula:

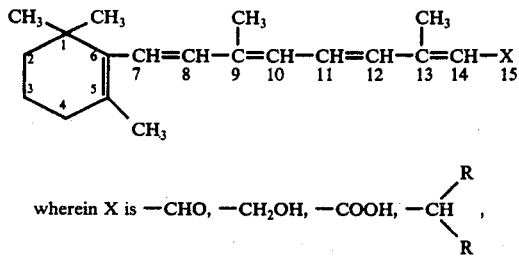

wherein X is —CHO, —CH$_2$OH, —COOH, —CH$\diagdown \diagup ^R_R$ ,

—CH$_2$OR$_1$, —COOR$_2$, —CONHR$_3$ or —CON(R$_3$)$_2$;
R is lower alkoxy or the two R's taken together form lower alkylenedioxy; R$_1$ is alkanoyl or aroyl;
R$_2$ is alkyl, aryl or aralkyl; and R$_3$ is hydroxy, alkyl, aryl or aralkyl;
either as an all trans isomer, a 9-cis isomer or a 11-cis isomer or as a mixture of these isomers can be isomerized by treating this composition with a palladium containing compound where the compound is other than palladium phthalocyanin or other than palladium containing compounds containing a cyanide group.

It has been found that in accordance with the present invention that, by isomerising pure all-trans, 9-cis or 11-cis isomers of compounds of formula I above or any isomeric mixtures thereof with palladium containing compounds, there is always obtained a mixture of isomers which consists of about 40–80% by weight (about 60–80% by weight in the case of vitamin A acetate) of all-trans compound, of about 10–30% by weight of 9-cis compound and at most about 3% by weight of 13-cis compound, and, when an aldehyde of formula I is used, at most about 20% by weight of 13-cis compound. The all-trans compound can be isolated from this mixture without difficulty, for example by simple crystallisation. It is even possible to obtain the practically pure all-trans compound by a single crystallisation from such a mixture which does not contain the 13-cis isomer or which contains only a small content (up to about 3–4% by weight) thereof.

Since the isomerisation of 11-cis compounds to all-trans compounds proceeds much quicker than the isomerisation of all trans compounds to 9-cis compounds, the amount of the latter, in the case where 11-cis compounds or isomer mixtures containing same are isomerised, is smaller than that given earlier in the aforementioned isomer mixture and can even lie below 10% by weight.

In accordance with the present invention, it is accordingly possible to increase the yield of all-trans compound in vitamin A synthesis or the purity of the end product since, in particular, the 9-cis isomer which is present in relatively large amounts in the reaction mixtures can be isomerised to the all-trans compound. Likewise, the present invention enables the use of synthesis which yield mainly the 9-cis isomer and which have not hitherto been used in practice since an adequate method for the conversion of the 9-cis isomer into the all-trans compound in accordance with customary methods has not been available.

A further advantage of the process provided by this invention is that it is now also possible, for example, to readily manufacture pure 9-cis vitamin A or 9-cis vitamin A acetate which have hitherto only been accessible by extremely complicated and expensive procedures. The manufacture of pure 9-cis vitamin A or 9-cis vitamin A acetate in accordance wth the present invention can be carried out, for example, as follows: pure vitamin A acetate is isomerised using a palladium containing compound. This is thereby obtained a mixture of all-trans and 9-cis vitamin A acetate as described hereinbefore, from which the all-trans isomer can be readily crystallized. The mother liquor remaining has a high content of 9-cis vitamin A acetate which can be converted into the corresponding alcohol and this alcohol crystallized. The pure 9-cis vitamin A alcohol can then be re-converted into the acetate if desired. Also if desired, the pure 9-cis vitamin A alcohol can be converted into the corresponding aldehyde or into the corresponding acid.

DETAILED DESCRIPTION

The numbering of the carbon atoms in the compound of formula I is shown for the purpose of convenience. The present invention relates to an isomerisation process.

As used in this application, the term "alkanoyl" means straight-chain and branched-chain alkanoyl groups containing from 1 to 18 carbon atoms (e.g. formyl, acetyl, propionyl, butyryl, stearoyl, palmitoyl and the like). Among the preferred alkanoyl groups are lower alkanoyl groups containing from 1 to 7 carbon atoms such as acetyl, butyl, propionyl, etc. The term "aroyl" means an aroyl groups which is preferably derived from an aromatic carboxylic acid containing from 7 to 11 carbon atoms (e.g. benzoyl). The term "alkyl" means a straight-chain or branched-chain alkyl group containing from 1 to 18 carbon atoms (e.g. methyl, ethyl, propyl, butyl, decyl, dodecyl, hexadecyl, octadecyl and the like). Among the preferred alkyl groups are lower alkyl groups containing from 1 to 7 carbon atoms such as methyl, ethyl, propyl, etc. The term "aryl" preferably means phenyl or naphthyl. The term "aralkyl" means aralkyl groups which contain from 1 to 4 carbon atoms in the aliphatic moiety (e.g. benzyl, phenylpropyl and the like). The term "lower alkoxy" means alkoxy groups containing from 1 to 6 carbon atoms (e.g. methoxy, ethoxy, propoxy and the like). The term "lower alkylenedioxy" means alkylenedioxy groups containing from 1 to 6 carbon atoms (e.g. methylenedioxy, ethylenedioxy and the like).

The isomerization process of this invention is preferably carried out with compounds of the formula I where X is —$CH_2OR_1$ or —CHO. Among the preferred compounds of formula I above where X is —$CH_2OR_1$ is the compound where $R_1$ is acetyl.

Where mixtures of compounds of formula I are used, these are preferably mixtures which contain 9-cis and all-trans vitamin A acetate and especially mixtures which contain from about 50% to about 70% by weight 9-cis vitamin A acetate and about 30% to about 50% by weight of all-trans vitamin A acetate. There are also preferred mixtures of 9-cis, 11-cis and all-trans vitamin A acetate, especially mixtures which contain from about 0% to about 15%, preferably 1% to 15%, by weight of 9-cis; from about 20% to about 40% by weight of 11-cis; an about 40% to about 70% by weight of all-trans vitamin A acetate.

The isomerisation in accordance with the present invention can be carried out catalytically in a homogeneous or heterogeneous system. The heterogeneous isomerisation can be carried out in the solid/liquid or liquid/liquid phase. It is also possible to carry out the isomerisation batch-wise or continuously.

The isomerisation is expediently carried out in an inert organic solvent. Any conventional inert organic solvent can be utilized in the process of this invention. Among the suitable solvents are the polar solvents, especially aprotic solvents such as, for example, acetonitrile, dimethylformamide and the like. Also, non-polar inert organic solvents are suitable. Among the preferred non-polar solvents are included aliphatic and aromatic hydrocarbons such as pentane, hexane, heptane, benzene, toluene, xylene, petroleum ether and the like. Halogenated aliphatic and aromatic hydrocarbon solvents such as methylene chloride, ethylene chloride, chloroform, carbon tetrachloride, chlorobenzene etc. can also be used. Another preferred solvents are the lower aliphatic alcohols such as methanol, ethanol, propanol etc. Mixtures of solvents can also be used.

It has been found that the isomerisation may be expediently carried out with the addition of water. The amount of water used can amount to about 5 vol. % to about 90 vol. %, preferably about 5 vol. % to about 50 vol. % and especially about 10 vol. % to about 20 vol. %, based on the total volume of the solvents used. In the case of a homogeneous catalytic isomerisation, it is preferred to utilize those solvents in which the palladium catalyst used for the isomerisation is soluble.

Where the catalyst used is only very slightly soluble or is very difficult to dissolve in a particular solvent, best yields are obtained by selecting a correspondingly longer isomerisation time. The isomerisation is conveniently carried out with the exclusion of air under an inert gas (e.g. nitrogen, argon etc.) and with the exclusion of light.

The isomerisation in accordance with the present invention can be conveniently carried out at a temperature of from about 0° C. to 250° C. The isomerisation is preferably carried out at a temperature from about 20° to about 150° C, especially from about 20° C. to about 100° C. It is particularly preferred to carry out the isomerisation at a temperature of from 20° C. to about 80° C.

For best results and highest conversions, isomerisation should be carried out for a period of from 1 minute to about 50 hours, especially from 15 minutes to about 10 hours and preferably from about 10 minutes to about 4 hours. In any event, the time of isomerisation is not critical in carrying out this isomerisation since isomerisation will occur upon contacting the compound of formula I with the palladium compound. However, the time of reaction to obtain best results and conversions will depend upon the palladium compound used, the solvent used and the temperature at which the isomerisation is carried out.

The palladium compound which is utilized to carry out the isomerization reaction of this invention can be any compound containing palladium except palladium phtalocyanin or palladium compounds which contain cyanide groups such as $Pd(CN)_2$, $K_2Pd(CN)_4$ and the like. These palladium compounds include not only palladium compounds such as palladium sulfide, palladium oxide and hydrates thereof but salts and complexes of palladium. The preferred palladium containing compounds are those compounds, salts and complexes of palladium where palladium has a value of zero, 2-[Pd(II)] or 4 [PD(IV)]. Certain types of palladium oxide are not active in themselves, but they can be readily activated by thermal treatment; for example, by heating under an inert gas for 1 hour at about 500° C.

The isomerisation reaction of this invention is preferably carried out using palladium compounds, namely Pd(O), Pd(II) or Pd(IV) salts or complexes, whereby these complexes can contain various types of ligands. Examples of such ligands are, in particular, halogens (e.g. fluorine, chlorine, bromine and iodine) or a halogen-like ligands such a thiocyanate; carboxylates (e.g. acetate, propionate, malonate etc.), nitrite, nitrate, sulphite, sulphate, thiosulphate, phosphites, i.e. alkylphosphites and arylphosphites (e.g. triethylphosphite, triphenylphosphite etc), trialkylphosphines and triarylphosphines (e.g. tributylphosphine, tricyclohexylphosphine, triphenylphosphine etc.), straight-chain or branched-chain alkyl groups (e.g. methyl, neopentyl etc.), aryl groups (e.g. phenyl etc.), branched-chain, straight-chain or cyclic olefins — the resulting complex can be a Pd-olefin or a Pd-allyl complex -, which can be unsubstituted or substituted by, for example, halogen, alkoxy, cyano etc, and in which the double-bonds, insofar as several are present, can be conjugated or non-conjugated such as alkenes and alkadienes (e.g. ethylene, propylene, butene, heptene, decene, butadiene, isoprene, cyclohexene, 1,5-cyclooctadiene etc) or alkatrienes (e.g. hexatriene) or alkatetraenes (e.g. cyclooctatetraene and the like), alkynes (e.g. acetylene, methylacetylene, dimethylacetylene, diphenylacetylene etc), primary, secondary and tertiary, saturated or unsaturated aliphatic or aromatic amines (e.g. ammonia, methylamine, dimethylamine, trimethylamine, ethylamine, diethylamine, triethylamine, pyridine, bipyridyl, quinoline etc), aliphatic or aromatic, substituted or unsubstituted nitriles (e.g. acrylonitrile, acetonitrile, propionitrile, butyronitrile, benzonitrile, succinic acid dinitrile and the like).

The following salts and complexes are preferred: $PdCl_2$, $PdBr_2$, $PdF_2$, $PdI_2$, $K_2PdCl_4$, $PdSO_4$, $K_2PdBr_4$, $(CH_3CN)_2PdCl_2$, $Pd(OAC)_2$, $(benzonitrile)_2PdCl_2$, $(benzonitrile)_2PdBr_2$, $(C_3H_5PdCl)_2$, $(cyclohexene-PdCl_2)_2$, $(1,5-cyclooctadiene)PdCl_2$, $(1,5-cyclooctadiene)PdBr_2$, $(1,5-cyclooctadiene)PdI_2$, $(cyclooctatetraene)PdBr_2$, $(acrylonitrile)_2PdCl_2$, $Pd(NO_3)_4(NH_4)_2$, $Pd(pyridine)_2(NO_2)_2$, $[N(CH_3)_3benzyl]_2Pd(NO_2)_4$, $Pd(NH_3)_2Cl_2$, $Pd(NH_3)_2(NO_2)_2$, $Pd(2,2-bipyridyl)Cl_2$, $(NH_4)_2PdCl_4$, $(NH_4)_2PdCl_6$, $PdS_2$, $K_2PdCl_6$, $(ethylenediamine)Pd(NO_2)_2$, $(amylamine)_2Pd(NO_2)_2$, $(NH_3)_4Pd(NO_3)_2$, $Pd(salicyclaldoxime)_2$, $(succinic\ acid\ dinitrile)PdCl_2$, $(cyclooctatetraene)PdCl_2$, $(azobenzene)_2PdCl_2$, $(bipyridyl)Pd(NO_2)_2$, $K_2Pd(malonate)_2$, $(tricyclohexylphosphine)_2PdCl_2$, $(triphenylphosphine)_2PdCl_2$, tetrakis-(triphenylphosphite)Pd(O), tetrakis-(triethylphosphite)Pd(O) and tetrakis-(triphenylphosphine)Pd(O).

A particularly preferred palladium compound for use in accordance with the present invention is palladium oxide.

In the case of a heterogeneous catalytic isomerisation, the catalyst can be used in the absence of a carrier material or it can be supported on a carrier material. The carrier material can be any of the customary carrier materials such as, for example, carbon, nickel oxide, aluminium oxide, barium sulphate, calcium carbonate, molecular sieves and the like. Certain polymers such as Nylon, Perlon and the like can also be used as the carrier material. There can also be used synthetic carrier materials which contain the ligands covalently bound thereto. The catalyst can be brought onto the carrier materials by conventional procedure. Where palladium oxide on a carrier material is used for the isomerisation, it is often necessary to activate the catalyst thermally, in the case of palladium oxide on nickel oxide for example by heating to ca 700° C. under an inert gas for 8 hours. The amount of palladium oxide on the carrier material can amount to 0.1% to 10% by weight to 90% to 99.9% by weight of carrier material. However, it is preferred to utilize the catalyst system containing palladium oxide in about 0.5% and about 6% by weight, preferably between about 0.5% and about 3% by weight.

The catalyst, i.e., the palladium compound used, can be employed in an amount of about 0.1 mol % to about 100 mol % based on the substrate to be isomerised. The catalyst is preferably employed in an amount of about 0.1 mol % to about 50 mol % or to about 20 mol %, and especially in an amount of about 1 mol % to about 10 mol %.

The isomerisation may, if desired, be conveniently carried out in the presence of a weak inorganic or an organic base. Especially suitable bases for this purpose are alkali metal carbonates and alkaline earth metal carbonates and oxides such as, for example, sodium carbonate, magnesium carbonate, calcium carbonate, magnesium oxide and the like. Organic bases which can be used are, in particular, primary, secondary and tertiary lower alkyl amines such as, for example, propylamine, diethylamine, triethylamine, tripropylamine and the like.

The following Examples are illustrative of the invention. In the Examples, all temperatures are in degrees centigrade. The petroleum ether utilized has a boiling point of 40°–45° C. The ether utilized in these examples is diethyl ether. The term dilute hydrochloric acid designates an aqueous solution containing about 10% by weight of hydrochloric acid. The term diluted sulphuric acid designates an aqueous solution contaning about 10% by weight of sulphuric acid.

EXAMPLE 1

7.5 mg. of $(benzonitrile)_2PdCl_2$ are dissolved in 4.5 ml. of benzene, 0.5 ml. of acetonitrile and 8 μl of tripropylamine at room temperature. To 2 ml. of this solution there are added at room temperature under argon and with the exclusion of light, 240 mg. of 9-cis vitamin A acetate and the mixture is heated at 65° C. for 2 hours. After cooling, the mixture is treated with 6 ml. of acetonitrile and extracted five times with 6 ml. of n-hexane each time. The combined hexane phases are evaporated at 40° C./12 mmHg and then at room temperature/$10^{-2}$ mmHg. There are obtained 220 mg. of an isomer mixture which contains 23% by weight 9-cis vitamin A acetate and 71.5% by weight all-trans vitamin A acetate. This isomer mixture (220 mg.) is dissolved in 400μ l of n-hexane at room temperature. The solution is cooled to −20° C. over a period of 4 hours and seeded at 0° C. with all-trans vitamin A acetate. The crystals obtained are separated and washed with 80 μl of n-hexane (−20° C.). The crystals are subsequently dried for 1 hour at room temperature in vacuo ($10^{-2}$ mmHg.). There are obtained 110 mg. of all-trans vitamin A acetate which is 99.6% by weight pure.

EXAMPLE 2

By the procedure of Example 1, a mixture of 95% by weight 11-cis vitamin A acetate and 5% by weight 11,13-di-cis vitamin A acetate is converted to an isomer mixture containing 21.8% 9-cis vitamin A acetate and 73.4% all-trans vitamin A acetate from which practically pure all-trans vitamin A acetate can be crystallised.

EXAMPLE 3

By the procedure of Example 1, a mixture of 12.5% by weight all-trans vitamin A acetate and 87.5% by weight 9-cis vitamin A acetate is converted to an isomer mixture consisting of 20.1% by weight 9-cis vitamin A acetate and 67.6% by weight all-trans vitamin A acetate from which practically pure vitamin A acetate can be crystallised.

EXAMPLE 4

In the following Tables there are compiled the results of further isomerisations using various catalysts, solvents, temperatures, isomerisation times and starting materials. The abbreviations used in these Tables are as follows:

VAAc = vitamin A acetate
VAAld = vitamin A aldehyde
TPA = tripropylamine
TAA = triethylamine.

The working-up of the isomer mixtures obtained can be carried out in a manner analogous to that described in Example 1. In the Tables, the amount of 9-cis compound, 13 cis compound and all trans compound is given in weight %.

| Starting material | Base | Catalyst | Solvent | Isomerisation time (in minutes) | Isomerisation temperature in °C | 9-cis compound | all-trans compound | 13-cis compound |
|---|---|---|---|---|---|---|---|---|
| 9-cis VAAc | TPA | PdCl₂ | Acetonitrile | 60 | 65 | 20.3 | 72 | |
| " | " | PdBr₂ | " | 15 | 65 | 23.3 | 72.5 | |
| " | " | K₂PdCl₄ | " | 60 | 65 | 20.3 | 73 | |
| " | " | K₂PdBr₄ | " | 60 | 65 | 21.2 | 72 | |
| all-trans VAAc | TAA | (Benzonitrile)₂ PdCl₂ | Benzene | 15 | 65 | 21.7 | 70.9 | |
| " | " | " | " | 240 | 50 | 20.8 | 71.6 | |
| " | " | " | " | 17 hours | Room temperature | 20.5 | 72.4 | |
| " | " | " | Acetonitrile | 15 | 65 | 20.6 | 73.1 | |
| " | " | " | " | 120 | 40 | 18.6 | 74 | |
| 9-cis VAAc | TAA | (Benzonitrile)₂ PdCl₂ | Acetonitrile | 15 | 50 | 24.3 | 67.2 | |
| all-trans VAAc | TPA | (Acetonitrile)₂ PdCl₂ | Benzene | 15 | 65 | 18.9 | 74.6 | |
| " | " | " | Acetonitrile | 15 | 65 | 20.4 | 73.1 | |
| 9-cis VAAc | " | (Cyclohexene PdCl₂)₂ | " | 15 | 65 | 22.9 | 72.1 | |
| " | " | (1,5-Cyclooctadiene) PdCl₂ | " | 15 | 65 | 23 | 76.1 | |
| " | " | (1,5-Cyclooctadiene) PdBr₂ | " | 20 | 50 | 21.2 | 72.3 | |
| " | " | " | " | 120 | 35 | 23.9 | 72.9 | |
| 9-cis VAAc | TPA | (Cyclooctatetraene) PdBr₂ | Acetonitrile | 15 | 50 | 23.7 | 68.7 | |
| " | " | (Acrylonitrile)₂ PdCl₂ | " | 15 | 65 | 21 | 73.2 | |
| all-trans VAAc | TAA | (C₃H₅-PdCl)₂ | " | 60 | 65 | 18.6 | 73.7 | |
| " | " | Pd(pyridyl)₂ (NO₂)₂ | " | 60 | 65 | 18.7 | 75.2 | |
| " | " | Pd(NO₃)₄ (NH₄)₂ | " | 60 | 65 | 20.3 | 72.6 | |
| " | " | Pd(OAc)₂ | " | 60 | 65 | 20.6 | 73.2 | |
| all-trans VA Ald | TAA | (Benzonitrile)₂ PdCl₂ | Acetonitrile | 5 | 65 | 10.5 | 78.3 | 7.2 |
| all-trans VA Ald | TAA | (Benzonitrile)₂ PdCl₂ | Acetonitrile | 60 | 65 | 18.8 | 67.5 | 6.8 |
| 9-cis VAAc | " | (NH₄)₂ PdCl₆ | " | 120 | 65 | 22.8 | 74.2 | |
| " | " | PdS₂ | " | 150 | 60 | 21.7 | 73.4 | |
| 9-cis VAAc | TPA | (Benzonitrile)₂ PdCl₂ | Dimethylformamide | 60 | 50 | 22 | 69 | |
| " | " | " | Toluene | 30 | 50 | 21 | 68 | |
| " | " | " | C₂H₄Cl₂ | 60 | 50 | 24 | 62 | |
| " | " | " | Chlorobenzene | 30 | 50 | 20 | 67 | |
| 9-cis VAAc | TAA | (Benzonitrile)₂ PdCl₂ | Acetone | 60 | 50 | 21 | 64 | |
| " | " | " | Diisopropyl ether | 90 | 50 | 22 | 69 | |
| " | " | " | Nitrobenzene | 60 | 50 | 20 | 67 | |
| " | " | " | CHCl₃ | 90 | 50 | 21 | 70 | |
| " | " | " | Ethyl acetate | 60 | 50 | 22 | 66 | |
| 11-cis VAAc | TPA | " | Acetonitrile | 240 | Room temperature | 12 | 72 | 2 |
| Mixture of 30% 11-cis and 70% all-trans VAAc | TPA | " | " | 180 | Room temperature | 7.1 | 78.3 | |
| all-trans VAAc | TPA | PdO 10 Mol. % activated for 1 hour at 500° C | Acetonitrile | 180 | 80 | 22 | 74 | |

-continued

| Starting material | Base | Catalyst | Solvent | Isomerisation time (in minutes) | Isomerisation temperature in ° C | 9-cis compound | all-trans compound | 13-cis compound |
|---|---|---|---|---|---|---|---|---|
| " | " | under argon " | " | 180 | 80 | 20 | 78 | |
| " | " | 1 Mol. % " | " | 180 | 80 | 17 | 79 | |
| 9-cis VAAc | " | " | " | 180 | 80 | 23 | 73 | |
| all-trans VAAc | " | 1% PdO/NiO 10 Mol. % activated for 8 hours at 700° C under argon | " | 180 | 80 | 21 | 65 | |
| " | " | " 1 Mol. % | " | 180 | 80 | 25 | 72 | |
| all-trans VAAc | TPA | (Ph$_3$P)$_2$ PdCl$_2$ | Aceto-nitrile + 10 Vol. % H$_2$O | 180 | 65 | 18.2 | 75.4 | |
| all-trans VA acid ethyl ester | TPA | Pd(NO$_3$)$_2$ | Aceto-nitrile | 60 | 65 | 22.2 | 77.5 | |
| " | TPA | (1,5-Cy-clooctadiene) PdCl$_2$ | " | 60 | 65 | 15.6 | 83.7 | |
| " | " | (CH$_3$CN)$_2$ PdCl$_2$ | " | 30 | 65 | 15 | 85.0 | |
| 9-cis VA aldehyde | TPA 2 Mol % | (Benzonitrile)$_2$ PdCl$_2$ | " | 60 | 65 | 22.7 | 70.5 | 5.9 |
| " | " | Pd(NO$_3$)$_2$ | " | 60 | 65 | 15.3 | 55.8 | 20 |
| " | " | (CH$_3$CN)$_2$ | " | 60 | 65 | 23.9 | 67.7 | 3.5 |
| 9-cis VA alcohol | TPA 2 Mol % | (CH$_3$CN)$_2$ PdCl$_2$ | Aceto-nitrile | 15 | 65 | 23.2 | 56.2 | |
| " | " | (1,5,-Cy-clooctadiene) PdCl$_2$ | " | 60 | 65 | 17.8 | 61.5 | |
| " | " | Pd(NH$_3$)$_2$Cl$_2$ | " | 60 | 65 | 18.6 | 57.2 | |

EXAMPLE 5

20 g. of a mixture of 61% by weight all-trans, 35.9% by weight 11-cis, 1.4% by weight 11,13-di-cis and 1% by weight 9-cis vitamin A acetate are dissolved in a solution of 120 ml. of acetonitrile/water (90% by volume acetonitrile and 10% by volume water) and 85 μl. of triethylamine (1 mol. % based on the isomer mixture), the solution is treated with 159 mg. of (CH$_3$CN)$_2$PdCl$_2$ (1 mol. % based on the isomer mixture) and the mixture is stirred at 50° C. for 7 hours. The mixture is then extracted four times with 120 ml. of n-hexane each time, the extract dried over sodium sulphate and evaporated. After drying for 2 hours in a high vacuum at room temperature, there are obtained 20.77 g. of a mixture containing 69.1% by weight all-trans, 19% by weight 9-cis and 0.2% by weight 11,13-di-cis vitamin A acetate.

This mixture (20.77 g.) is crystallised from 20 ml. of n-hexane, there being obtained 8.56 g. of mother liquor as well as 11.01 g. of crystals containing 99.2% by weight all-trans and 0.6% by weight 9-cis vitamin A acetate.

The mother liquor (8.56 g.) is dissolved in the aforementioned isomerisation mixture, stirred for 1 hour at 50° C. and then extracted and dried in the manner previously described. There are obtained 8.4 g. of a mixture containing 67.8% by weight all-trans and 20.5% by weight 9-cis vitamin A acetate.

This mixture (8.4 g.) is crystallised from 8.5 ml. of n-hexane, there being obtained a further 4.08 g. of crystals consisting of 99.3% by weight all-trans and 0.7% by weight 9-cis vitamin A acetate as well as 4.22 g. of mother liquor containing 41.4% by weight all-trans, 40.4% by weight 9-cis, 1.5% by weight, 11,13-di-cis, 0.4% by weight 11-cis and 0.4% by weight 13-cis vitamin A acetate. To the first of the aforementioned isomerisation mixtures are added 85 μl. of triethylamine, the mother liquor (4.22 g.) is dissolved therein, the mixture is stirred at 50° C. for one hour and then extracted and dried as described previously. There are obtained 3.86 g. of a mixture containing 58.6% by weight all-trans, 18% by weight 9-cis and 0.6% by weight 13-cis vitamin A acetate.

This mixture (3.86 g.) is crystallised from 4 ml. of n-hexane, there being obtained a further 1.5 g. of crystals containing 98.7% by weight all-trans and 0.5% by weight 9-cis vitamin A acetate.

All analyses were carried out by liquid chromatography.

EXAMPLE 6

1780 g. of all-trans vitamin A acetate are dissolved in 3600 ml. of hexane with the addition of 1 ml. of triethylamine. After the addition of 1.8 g. of (benzonitrile)$_2$PdCl$_2$, the mixture is stirred under nitrogen and with the exclusion of light at 60°–65° C. for 20 hours. The mixture is then slowly cooled to 0° C. with stirring. After seeding with all-trans vitamin A acetate, the mixture is then slowly cooled to −40° C. The all-trans vitamin A acetate which thereby crystallises is filtered over a suction filter pre-cooled with dry-ice and the crystallisate is washed three times with a total of 1800 ml. of hexane at −70° C. The still moist all-trans vitamin A acetate is again isomerised according to the method described earlier. The filtrates obtained after four isomerisations are combined and evaporated in vacuo at room temperature. In this manner, there are obtained 1380 g. of a 9-cis/all-trans vitamin A acetate mixture.

500 g. of the foregoing mixture are dissolved under nitrogen in 1650 ml. of ethanol and the solution is warmed to 40° C. At this temperature, there is added dropwise over a period of 15 minutes a solution of 185 g. of sodium hydroxide in 770 ml. of water. The mixture is subsequently stirred for a further 30 minutes at 40° C. The mixture is then cooled to 10° C. and extracted with 1600 ml. of petroleum ether. The separated aqueous phase is extracted a further twice with 500 ml. of petroleum ether each time. The organic phases are washed neutral with ice-water, dried and evaporated. There are obtained 450 g. of a yellow oil which is dissolved in 900 ml. of methyl formate with the addition of 1.8 ml. of pyridine. The solution is cooled to $-5°$ C. while stirring over a period of 2 hours, seeding with 9-cis vitamin A alcohol being carried out at 10° C. The crystallised product is filtered under suction over a suction filter pre-cooled with dry-ice and the crystallisate washed in small portions with a mixture of 900 ml. of methyl formate and 0.9 ml. of pyridine at $-70°$ C. The product, which is now colorless, is dried in vacuo at room temperature. There are obtained 209 g. of 9-cis vitamin A alcohol of melting point 82°-83° C.

a. 209 g. of 9-cis vitamin A alcohol are dissolved under nitrogen in a mixture of 1000 ml. of absolute benzene and 176 ml. of pyridine. The mixture is cooled in $-10°$ C. and, at this temperature, there is added dropwise with stirring over a period of 1 hour a solution of 78.2 ml. of acetyl chloride in 400 ml. of absolute benzene. After the addition, the mixture is stirred for a further 2 hours at room temperature. The mixture is then poured on to icewater and the organic phase extracted three times with water, dried and evaporated in vacuo at room temperature. The residual pyridine is removed under a high vacuum. There are obtained 254 g. of a yellow oil. This oil is filtered under nitrogen and with the exclusion of light over 1 kg. of silica gel using a mixture of petroleum ether and diethyl ether (4:1 parts by volume). The filtrate is evaporated and the product dried under a high vacuum. There are obtained 225 g. of pure 9-cis vitamin A acetate.

b. 50 g. of 9-cis vitamin A alcohol are dissolved in 500 ml. of methylene chloride and stirred for 24 hours under nitrogen and with the exclusion of light with 300 g. of manganese dioxide at room temperature. The manganses dioxide is filtered off in vacuo and rinsed with 300 ml. of methylene chloride. The filtrate is evaporated in vacuo. The crystalline residue is dissolved in 150 ml. of petroleum ether with slight warming and cooled to $-40°$ C. over a period of 30 minutes. The aldehyde which thereby crystallises is rapidly filtered off under suction over a suction filter pre-cooled with dry-ice and the crystallisate is washed three times with 80 ml. of petroleum ether at $-70°$ C. each time. After drying the product in vacuo at room temperature, there are obtained 40 g. of 9-cis vitamin A aldehyde of melting point 63°-64° C. The mother liquor is concentrated and, by crystallisation, there are obtained a further 2.8 g. of 9-cis vitamin A aldehyde of melting point 62°-63° C.

c. 10 g. of 9-cis vitamin A aldehyde are dissolved in 100 ml. of methanol and 100 ml. of tetrahydrofuran. This solution is added dropwise to a fine aqueous suspension of silver oxide. The mixture is subsequently stirred for 12 hours at room temperature. The precipitated silver is filtered off from the mixture and the filtrate evaporated to ca 100 ml. After the addition of 250 ml. of water, the mixture is extracted three times with 100 ml. of diethyl ether each time. The ether phases are then washed twice with 50 ml. of water each time. The combined aqueous phases are acidified with dilute sulphuric acid while cooling with ice and extracted three times with 100 ml. of diethyl ether each time. The ether phases are washed with water, dried and evaporated. The residue is dissolved in 50 ml. of diethyl ether with warming and this solution is slowly cooled to $-40°$ C. while stirring. The 9-cis vitamin A acid which thereby crystallises is filtered off under suction over a suction filter pre-cooled with dry-ice, the crystallisate is rinsed with 10 ml. of diethyl ether at $-70°$ C. and dried in vacuo at room temperature. There are obtained 6.4 g. of 9-cis vitamin A acid of melting point 188°-190° C.

EXAMPLE 7

By the procedure described in Example 1, all-trans vitamin A acetate is converted into a mixture containing 75% by weight all-trans vitamin A acetate and 11% by weight 9-cis vitamin A acetate over a period of 3 hours at 80° C. in acetonitrile containing 10% by weight water. The isomerisation catalyst consists of 10 mol. % palladium on a mixed polymerisate of styrene and divinylbenzene with benzyldiphenylphosphine.

EXAMPLE 8

1 g. of 9-cis vitamin A acetate is dissolved in 5 ml. of acetonitrile. After the addition of 0.5 g. of one of the following catalysts:
  a. $PdO/BaSO_4$;
  b. PdO/molecular sieves;
  c. $PdO/CaSO_4$
(2% Pd on carrier material), the mixture is heated at 70° C. for one hour while stirring. After cooling the mixture, the catalyst is filtered off and the filtrate evaporated in vacuo at room temperature. The respective isomer mixtures obtained have the following compositions (all % are % by weight):
  a. 72% all-trans and 28% 9-cis vitamin A acetate;
  b. 68% all-trans and 32% 9-cis vitamin A acetate;
  c. 71% all-trans and 92% 9-cis vitamin A acetate.

EXAMPLE 9

1 g. of 9-cis vitamin A acetate is dissolved in 5 ml. of acetonitrile. Thereafter, a $PdO/BaSO_4$ catalyst having the Pd concentrations given in the Table hereinafter is added in such a manner that the Pd content based on the substrate amounts to 1% by weight in each case. The mixture is heated at 70° C. for one hour while stirring. After cooling, the catalyst is filtered off and the filtrate evaporated in vacuo. The thus-obtained vitamin A acetate isomer mixture has a total acetate content of ca 99-100% by weight and an isomer ratio given in the following Table:

| $PdO/BaSO_4$ Pd content on carrier material in % by weight | all-trans in % by weight | 9-cis in % by wt. |
|---|---|---|
| 0.5 | 75 | 25 |
| 1 | 75 | 25 |
| 2 | 74 | 26 |
| 3 | 73 | 27 |

TABLE 10

20 g. of PdO/BaSO₄ catalyst containing 0.5% Pd on the carrier material are introduced into a glass column heated at 70° C. 10 g. of a 9-cis/all-trans vitamin A acetate mixture in the ratio 60:40% by weight, dissolved in 30 ml. of acetonitrile, is allowed to pass dropwise through this column filled with the catalyst. A further 50 ml. of acetonitrile are then added. In this manner, there are obtained after evaporation of the filtrate, 9 g. of a 9-cis/all-trans vitamin A acetate mixture in the ratio 29:71% by weight.

EXAMPLE 11

3 g. of a 9-cis/all-trans vitamin A acetate isomer mixture in the ratio 60:40% by weight are dissolved in 15 ml. of a mixture of heptane and acetonitrile in the ratio given in the Table hereinafter. After the addition of 6 g. of PdO/BaSO₄ catalyst containing 0.5% by weight Pd on the carrier material, the mixture is heated at 70° C. for one hour while stirring. After cooling the mixture, the catalyst is filtered off and the filtrate evaporated in vacuo. The resulting vitamin A acetate isomer mixture has the isomer ratio given in the following Table (all % unless otherwise designated, are % by weight).

| heptane/acetonitrile solvent Vol. % | | all-trans in % | 9-cis in % |
|---|---|---|---|
| 0 | 100 | 76 | 24 |
| 50 | 50 | 75 | 25 |
| 75 | 25 | 74 | 26 |
| 90 | 10 | 74 | 26 |
| 95 | 5 | 73 | 27 |
| 99 | 1 | 71 | 29 |

EXAMPLE 12

1 g. of 9-cis vitamin A acetate is dissolved in 5 ml. of one of the solvents listed in the following Table. After the addition of 2 g. of PdO/BaSO₄ catalyst (0.5% by weight Pd on carrier material), the mixture is stirred at 70° C. for one hour. After cooling the mixture, the catalyst is filtered off and the filtrate evaporated. The resulting vitamin A acetate isomer mixture has the isomer ratio given in the following Table (all % are in % by weight):

| Solvent | all-trans in % | 9-cis in % |
|---|---|---|
| Acetonitrile | 75 | 25 |
| Ethanol | 72 | 28 |
| Propanol | 70 | 30 |

EXAMPLE 13

The following Example illustrates the manner in which the PdO/carrier material catalysts used in the foregoing Examples can be prepared:

78.4 g. of BaSO₄ are suspended with intensive stirring in 300 ml. of de-ionised water at 20° C. A solution of 2.66 g. of PdCl₂ in 100 ml. of dilute hydrochloric acid is added over a period of 5 minutes while stirring. The brown color of the palladium chloride solution disappears immediately upon the dropwise introduction into the barium sulphate suspension. The acidic solution is then adjusted to pH 8–9 by dropwise treatment with 2-N aqueous sodium hydroxide. After stirring for a further 5 minutes, the catalyst is left to settle and the supernatant clear solution is decanted off. The catalyst is again suspended in de-ionised water and filtered over a sintered glass filter. It is then washed halogen-free with de-ionised water and the suction-dried catalyst then dried in a vacuum drying oven at 80°–92° C./12 mmHg over a period of ca 15 hours.

The dried and ground catalyst can be used for the isomerisation without further treatment.

We claim:

1. A process for geometrically isomerizing an isomeric composition selected from the group consisting of 9-cis and 11-cis isomers of a compound of the formula:

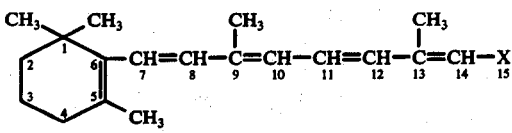

wherein X is

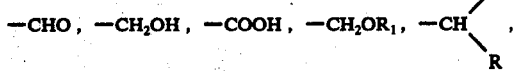

—COOR₂, —CONHR₃ or —CON(R₃)₂; R is lower alkoxy or the two R's taken together form lower alkylenedioxy; R₁ is alkanoyl or aroyl; R₂ is alkyl, aryl or aralkyl; and R₃ is hydroxy, alkyl, aryl or aralkyl; mixtures thereof, or mixtures thereof with the all trans isomer of said compound comprising contacting at a temperature of from 0° C to 250° C; said composition in an inert solvent medium with a palladium compound catalyst where the palladium compound is other than palladium phthalocyanin or other than a palladium compound containing a cyanide ion and producing a geometric isomeric mixture of said composition from which the all trans isomer can be separated therefrom in pure form by crystallization.

2. A process of claim 1, wherein the isomerisation is carried out using Pd(O), Pd(II), or PD(IV) salts or complexes.

3. A process of claim 1, wherein the isomerisation is carried out using palladium oxide.

4. A process of claim 3, wherein the isomerisation is carried out using palladium oxide on a carrier material.

5. The process of claim 1, wherein the mixture contains from about 0% to about 15% by weight of 9-cis vitamin A acetate and from about 20% to about 40% by weight 11-cis vitamin A acetate and from about 40% to about 70% by weight all-tras vitamin A acetate based on the total weight of vitamin A acetate.

6. The process of claim 2, wherein the palladium compound is selected from the group consisting of a Pd(II) complex which contains a ligand selected from the group consisting of halogens, carboxylates, nitrite, nitrate, olefins, amines or nitriles.

7. The process of claim 6, wherein the Pd(II) complex contains alkadienes or alkatetraenes as the olefinic ligands.

8. The process of claim 7 wherein (1,5-cyclooctadiene)PdCl₂, (1,5-cyclooctadiene)PdBr₂, (1,5-cyclooctadiene)PdI₂ or (cyclooctatetraene)-PdBr₂ is the Pd(II) complex.

9. The process of claim 6 wherein (benzonitrile)₂PdCl₂, (acetonitrile)₂PdCl₂ or (acetonitrile)₂PdBr₂ is the Pd(II) complex.

10. The process of claim 1 wherein said palladium compound is a Pd(IV) composition selected from the group consisting of $PdS_2$ or $(NH_4)_2PdCl_6$.

11. The process of claim 1 wherein the isomerisation is carried out in a polar aprotic solvent or in a non-polar solvent.

12. The process according to claim 11 wherein the isomerisation is carried out with the addition of water.

13. The process of claim 1, wherein the isomerisation is carried out at a temperature of from 20° C. to about 80° C.

14. The process according to claim 1 wherein the catalyst is used in an amount of about 0.1 mol. % to about 100 mol. % based on the isomeric composition to be isomerised.

15. The process of claim 14 wherein the catalyst is used in an amount of about 1 mol. % to about 10 mol. % based on the isomeric composition to be isomerised.

* * * * *